(12) United States Patent
Kurtz et al.

(10) Patent No.: US 8,075,552 B2
(45) Date of Patent: Dec. 13, 2011

(54) SYSTEM AND METHOD FOR PREPARATION OF DONOR CORNEAL TISSUE

(75) Inventors: Ronald M. Kurtz, Irvine, CA (US); Melvin A. Sarayba, Ladera Ranch, CA (US); Michael Brownell, San Clemente, CA (US)

(73) Assignee: AMO Development LLC., Santa Ana, CA (US)

( * ) Notice: Subject to any disclaimer, the term of this patent is extended or adjusted under 35 U.S.C. 154(b) by 1423 days.

(21) Appl. No.: 11/561,849

(22) Filed: Nov. 20, 2006

(65) Prior Publication Data

US 2008/0119827 A1    May 22, 2008

(51) Int. Cl.
*A61F 9/008* (2006.01)
(52) U.S. Cl. .......................... 606/4; 128/898
(58) Field of Classification Search .................. 128/898; 606/4–5
See application file for complete search history.

(56) References Cited

U.S. PATENT DOCUMENTS

| 4,887,592 | A | * | 12/1989 | Loertscher | 606/5 |
| 5,647,865 | A | * | 7/1997 | Swinger | 606/5 |
| 2006/0020259 | A1 | | 1/2006 | Baumeister et al. | |
| 2007/0282313 | A1 | * | 12/2007 | Huang et al. | 606/5 |
| 2008/0114386 | A1 | * | 5/2008 | Iliakis et al. | 606/166 |

OTHER PUBLICATIONS

International Search Report and Written Opinion of PCT Application No. PCT/US07/85136, dated Jun. 26, 2008, 7 pages total.

* cited by examiner

*Primary Examiner* — Henry M Johnson, III

(57) ABSTRACT

A system and method for preparation of donor corneal tissue is disclosed. The system includes two surgical lasers. The first surgical laser is adapted to incise a recipient cornea to enable resection of recipient corneal tissue. The second surgical laser is adapted to incise a donor cornea to enable resection of donor corneal tissue. Both surgical lasers are adapted to make corneal incisions which are defined by incision parameters. Further, both surgical lasers are calibrated to make substantially precise corneal incisions when provided with identical incision parameters.

8 Claims, 2 Drawing Sheets

SYSTEM AND METHOD FOR PREPARATION OF DONOR CORNEAL TISSUE

BACKGROUND OF THE INVENTION

1. Field of the Invention

The field of the present invention is systems and procedures for transplanting corneas.

2. Background

Corneal transplants using lasers to incise corneal tissue prior to transplantation of donor tissue into the cornea of a recipient cornea are relatively new procedures. As part of these procedures, laser incisions are made in both the donor cornea and the recipient cornea. Most lasers used for such transplant procedures have dual uses—they have been employed as part of LASIK procedures for several years, typically to incise the cornea and provide surgeons with access to stromal tissue within the cornea. Such lasers are typically housed right in the ophthalmologist's office or in a surgical center for refractive eye care because, up until recently, the primary use of these lasers has been for performing the LASIK procedure. These offices and centers, however, are not generally kept in the sterile condition required for corneal transplant procedures. They generally lack the equipment and expertise to maintain tissue sterility, to verify the health of tissues following laser incisions, and to conform to mandated controls and safe practices for tissue handling prior to and during a transplant procedure. While the equipment, expertise, and controls could be installed in such offices and centers, there is little incentive, monetary or otherwise, to do so given the overall low volume of transplant procedures that are actually performed.

SUMMARY OF THE INVENTION

The present invention is directed toward a system and method for preparation of donor corneal tissue. The system includes two surgical lasers, the first of which is adapted to incise a recipient cornea to enable resection of recipient corneal tissue. The second surgical laser is adapted to incise a donor cornea to enable resection of donor corneal tissue. Both surgical lasers are adapted to make corneal incisions defined by incision parameters, and both are calibrated to make substantially precise incisions when provided with identical incision parameters. Preferably, each of the surgical lasers are calibrated to make the corneal incisions to within a predetermined tolerance.

The system may be configured to include one or more options. As a first option, the first surgical laser is configured to transmit the selected incision parameters to the second surgical laser. The transmission may be performed through a communication network, public or private, or through a direct connection between the tow surgical lasers. As a second option, at least one of the surgical lasers may be adapted to provide selectable options which enable the operator to alter one or more of the corneal incisions defined by the incision parameters according to predetermined alteration parameters. Such an option permits select incisions to be made oversized or undersized as desired by the attending surgeon.

In the method, two surgical lasers are first calibrated such that they make substantially precise incisions in corneal tissue when provided with identical incision parameters. Next, the first surgical laser, which is adapted to incise a recipient cornea, provides a plurality of incision parameters for selection of first incision parameters. The first incision parameters are used to incise the recipient cornea to enable resection of recipient corneal tissue. The first incision parameters are also transferred to the second surgical laser for incising the donor cornea, thereby enabling resection of donor corneal tissue. The method may also be altered to include one or more of the configuration options discussed above for the system.

Accordingly, an improved system and method for preparation of donor corneal tissue are disclosed. Advantages of the improvements will appear from the drawings and the description of the preferred embodiment.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
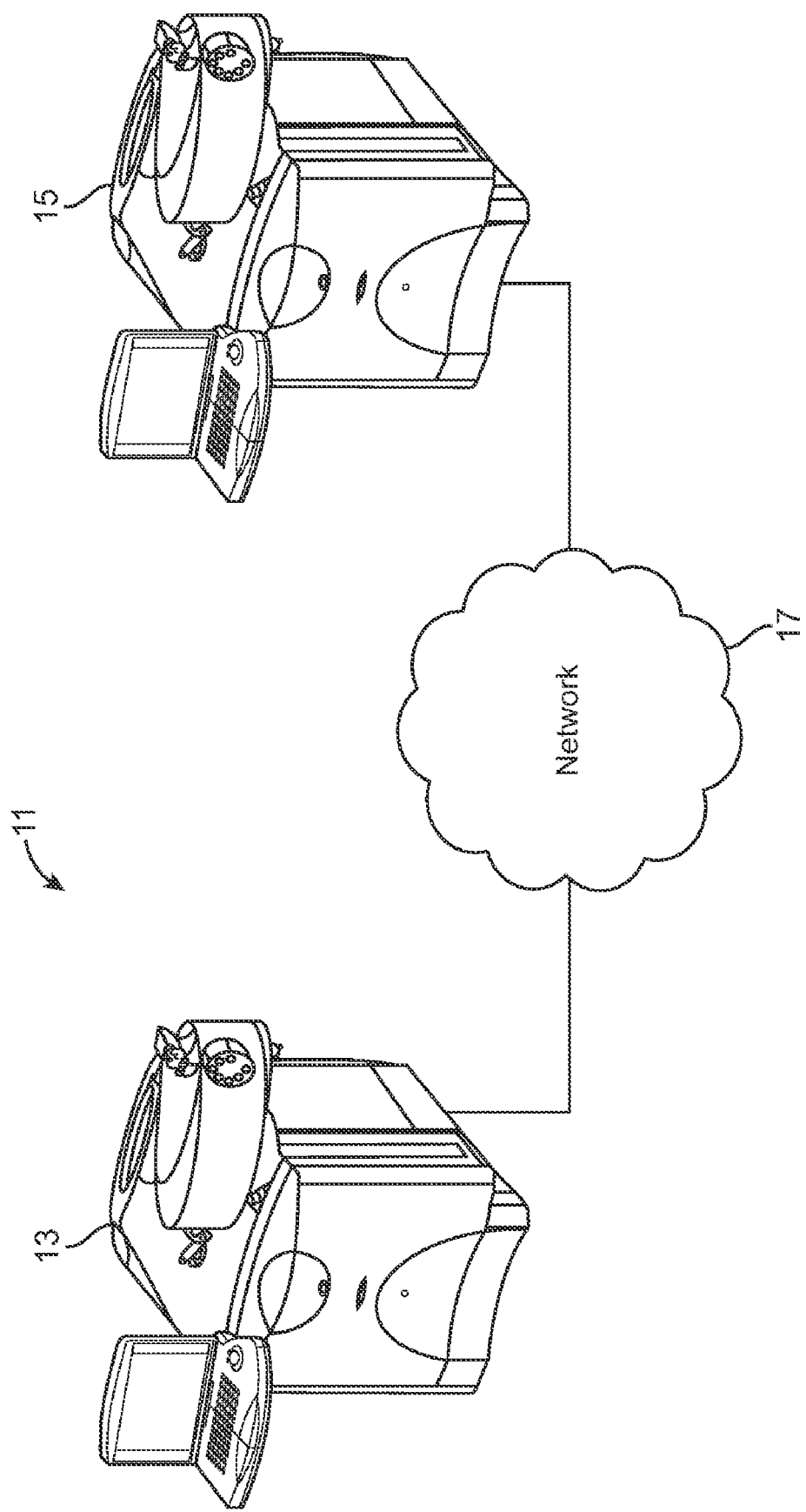
FIG. 1 schematically illustrates a system for preparation of donor corneal tissue.

Turning in detail to the drawings, FIG. 1 illustrates a system 11 for preparation of donor corneal tissue as part of a transplant procedure. The system 11 has two primary components, a first surgical laser 13 and a second surgical laser 15, both of which are interconnected to communicate via a communication network 17. Each surgical laser preferably has surgical capabilities similar to commercially available femtosecond surgical lasers, such as the surgical laser manufactured by IntraLase Corp. of Irvine, Calif. These surgical lasers are capable of being programmed with various incision patterns, or alternatively incision pattern segments which may be used to construct a whole incision pattern, for incising corneal tissue. By including preprogrammed incision patterns with the surgical laser, the attending surgeon may be provided with choices for selection of an appropriate incision pattern for a given transplant procedure.

The two surgical lasers may be located within the same surgical facility. However, the system 11 shown in FIG. 1 is suited to have the surgical lasers located at separate, remote locations. For example, the first surgical laser 13 might be located at the facilities where the surgeon will perform the graft itself, and the second surgical laser 15 might be located at a tissue bank where the donor cornea is prepared and processed so that the donor corneal tissue can be harvested. The network 17 may be a public or private communication network, such as the Internet, or it may be a direct connection between the two surgical lasers using a telephone service. In essence, the communication network may be any type of network, digital or analogue, known to those skilled in the art of electronic communication networks.

In order to ensure that the two surgical lasers 13, 15 are capable of being used in combination for a successful transplant procedure, they both need to be calibrated so that an incision is made with precision to within a predetermined tolerance as compared the definition of the incision according to the incision parameter. With proper calibration, both surgical lasers 13, 15 are capable of making incisions in the direction of the z-axis (the z-axis runs along the optical axis of the laser beam emitted from the surgical laser) and within planes perpendicular to the z-axis (i.e., planes defined by the x-axis and y-axis, each being orthogonal to the z-axis) with substantially the same precision. Such precision allows the both surgical lasers 13, 15 to make substantially the same cut, with the same amount of precision, when provided with identical incision parameters.

Calibration along each axis direction helps ensure that the two surgical lasers 13, 15 make incisions at substantially the same depth within the cornea and having substantially the same shape. Making a corneal incision with depth precision can be important for many different types of incision patterns, especially for incisions which run anterior to posterior, and not in a straight line, within the cornea. An example of a non-straight incision is a "zigzag" incision, which is described in U.S. patent application Ser. No. 11/469,899, filed Sep. 5, 2006, the disclosure of which is incorporated herein by reference. Making incisions at a precise depth is also important during transplant procedures such as the anterior lamellar keratoplasty (ALK) or the posterior lamellar keratoplasty (PLK), each of which involves a partial thickness corneal transplant.

Similarly, making a corneal incision with precision in the x-axis and y-axis directions can be important for matching the overall size of donor corneal tissue to the recipient cornea. Typically, the surgeon will elect to remove recipient corneal tissue using a simple radial incision to define the perimeter of the damaged tissue to be replaced. For such procedures, it is highly desirable that the radius of the donor corneal tissue closely match, to within a predetermined tolerance, the radius of the damaged tissue removed from the recipient cornea. For other transplant procedures, the surgeon may elect to make more complex incisions, such as an ellipse or other, even more complex shape, to define the perimeter of the damaged tissue to be removed. The complexity of the incision may be as complex as desired and may take any form selected by the attending surgeon. Again, regardless of how the periphery of the graft is defined by the surgeon, it is highly desirable that the perimeter of the donor corneal tissue closely match, to within a predetermined tolerance, the perimeter of the damaged tissue removed from the recipient cornea.

In order to ensure that the incisions in both the donor cornea and the recipient cornea are made to within the predetermined tolerance, both surgical lasers 13, 15 are calibrated in advance. Calibration of the lasers may be performed using any technique known to the skilled artisan. One method of calibration includes directing the laser beam from the surgical laser into a substrate, such as glass, agarose gel, or other appropriate material, to make test patterns at predetermined depths within the substrate. The test patterns are selected to allow calibration along all three major axes. The precision of the test patterns and the depth of each test pattern is thereafter measured to determine the overall precision of the surgical laser. Once the precision is known, the optics of the laser may be adjusted to increase the precision, or more preferably, the programming of the laser is adjusted to compensate for any measured imprecision, thereby enabling the surgical laser make more precise incisions. Preferably, the each surgical laser is calibrated to have a precision which is better than 200 μm in the direction of the x-axis and y-axis and better than 20 μm in the direction of the z-axis, although depending upon the needs of the surgeon, the precision of each surgical laser may be as much as 500 μm or as little as 25 μm in the direction of the x-axis and y-axis or as much as 50 μm or as little as 5 μm in the direction of the z-axis. These calibration steps may be repeated as necessary until the desired level of precision is attained for each surgical laser.

Figure 2:
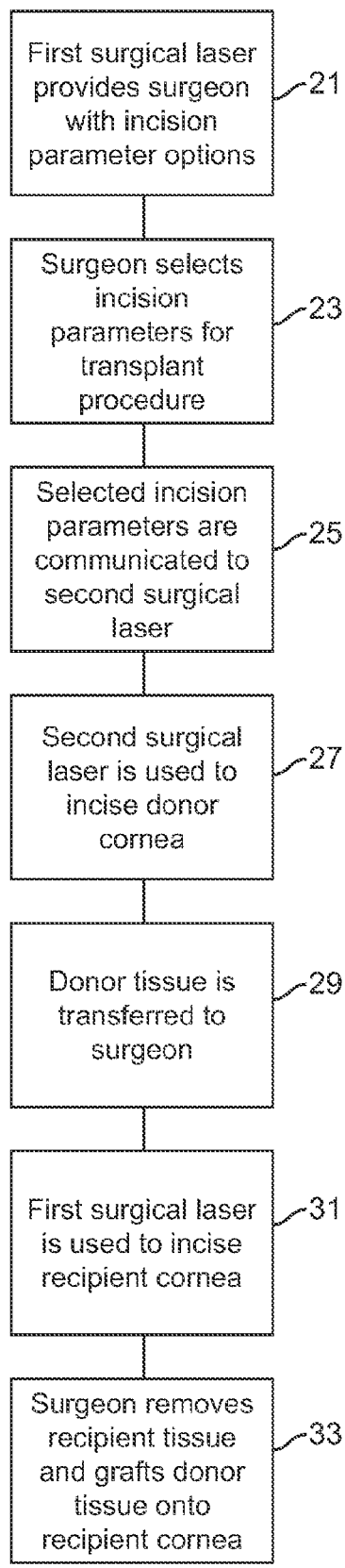
FIG. 2 is a flowchart showing the steps of a transplant procedure.

Following calibration, FIG. 2 shows the basic steps taken to perform a transplant procedure using the two surgical lasers of FIG. 1. In the first step 21, the first surgical laser presents the surgeon with various options for the incision parameters. Preferably, the surgeon is the one performing the transplant procedure and the first surgical laser is the one used to incise the recipient cornea. These options may include an entire incision pattern sufficient to allow resection of corneal tissue, or they may be segments of incision patterns which, when properly selected and assembled into a whole incision pattern, are sufficient to allow resection of corneal tissue. In the second step 23, the surgeon selects an incision pattern, or segments of incision patterns, which forms the basis of the incision parameters for the transplant procedure. In addition to the pattern, the surgeon also selects as part of the incision parameters dimensions of the corneal tissue which is to be removed from both the donor and recipient corneas. In the next step 25, the selected incision parameters are communicated to the second surgical laser. Other data may also be included as part of the incision parameters at the discretion of the surgeon. This communication may occur electronically between the two surgical lasers over a communication network as shown in FIG. 1, or it may be done in a more manual fashion, where the incision parameters are placed in writing, transferred to the facility housing the second surgical laser, and manually input into the second surgical laser.

Once the incision parameters are transferred to the second surgical laser, the next step 27 is to use the second surgical laser to incise the donor cornea. After the donor cornea is incised, in the next step 29 the donor tissue is transported to the facility where the surgeon is performing the transplant procedure. The donor tissue may be resected from the donor cornea before transport to the surgeon, or alternatively, the entire donor cornea may be transported to the surgeon, who then resects the donor tissue from the donor cornea prior to or at the time of the transplant procedure. Following receipt of the donor tissue, the next step 31 is for the surgeon to incise the recipient cornea so that the in the last step 33, the recipient tissue is resected and the donor tissue is grafted into the recipient cornea.

Another option which may be made available to the surgeon overseeing the transplant procedure is the option to have one of the surgical lasers make incisions oversized or undersized. This permits the surgeon to better manage the relative sizes of the donor tissue and the incision made in the recipient cornea to achieve a better fit for the grafted tissue. For example, the surgeon may elect to alter select incisions in the incision pattern for the donor cornea so that the select incisions are slightly oversized (or undersized) as compared to the same incisions made in the recipient cornea. Such alterations are preferably identified as alteration parameters which are transmitted as part of the incision parameters to the surgical laser that incises the donor cornea. These alterations may be applied to any part of the incision pattern, including but not limited to the overall size of the perimeter of the incision pattern, the depth of any angles formed by the incision pattern, or the depth of any stromal bed which is formed as part of an ALK or PLK procedure. Similarly, the surgeon may choose to make select incisions in the recipient cornea oversized or undersized using the first surgical laser and have the second surgical laser incise the donor cornea according unaltered incision parameters.

Thus, a system and method for preparation of donor corneal tissue are disclosed. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A method of preparing donor corneal tissue for transplantation, the method comprising:

calibrating a first surgical laser and a second surgical laser, wherein both the first surgical laser and the second surgical laser are adapted to make corneal incisions defined by incision parameters and, when calibrated, are adapted to make substantially precise incisions when provided with identical incision parameters;

providing a plurality of incision parameters for identification of first incision parameters, wherein the first surgical laser is adapted to incise the recipient cornea according to the first incision parameters;

transferring the first incision parameters to the second surgical laser; and incising the donor cornea according to the first incision parameters using the second surgical laser to enable resection of donor corneal tissue.

2. The method of claim 1, wherein transferring the first incision parameters includes transmitting the first incision parameters to the second surgical laser.

3. The method of claim 2, wherein transmitting the first incision parameters includes transmitting the first incision parameters over a communication network.

4. The method of claim 1, wherein incising the donor cornea includes providing options to alter one or more of the corneal incisions defined by the first incision parameters according to predetermined alteration parameters.

5. The method of claim 1 further comprising incising the recipient cornea according to the first incision parameters using the first surgical laser to enable resection of recipient corneal tissue.

6. The method of claim 5, wherein incising the recipient cornea includes providing options to alter one or more of the corneal incisions defined by the first incision parameters according to predetermined alteration parameters.

7. A method of transplanting corneal tissue, the method comprising:

calibrating a first surgical laser and a second surgical laser, wherein both the first surgical laser and the second surgical laser are adapted to make corneal incisions defined by incision parameters and, when calibrated, are adapted to make precise incisions, when provided with identical incision parameters, to within a predetermined tolerance;

providing a plurality of incision parameters for identification of first incision parameters, wherein the first surgical laser is adapted to incise the recipient cornea according to the first incision parameters;

transmitting the first incision parameters to the second surgical laser;

providing a plurality of alteration parameters for identification of first alteration parameters, wherein the second surgical laser is adapted to alter the first incision parameters according to the first alteration parameters;

incising the donor cornea according to the altered first incision parameters, using the second surgical laser, to enable resection of donor corneal tissue;

incising the recipient cornea according to the first incision parameters, using the first surgical laser, to enable resection of recipient corneal tissue;

resecting the donor and recipient corneas; and grafting the donor corneal tissue into the recipient cornea.

8. The method of claim 7, wherein transmitting the first incision parameters includes transmitting the first incision parameters over a communication network.

* * * * *